United States Patent
Shreve et al.

(10) Patent No.: US 10,399,031 B2
(45) Date of Patent: Sep. 3, 2019

(54) REGULATOR FOR IMPROVED THERMAL AND PRESSURE CONTROL FOR CHROMATOGRAPHY

(71) Applicant: Waters Technologies Corporation, Milford, MA (US)

(72) Inventors: Joshua A. Shreve, Franklin, MA (US); John Maillet, Jr.; Steven D. Trudeau, Webster, MA (US); Paul Linderson, Warwick, RI (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 608 days.

(21) Appl. No.: 14/381,981

(22) PCT Filed: Mar. 7, 2013

(86) PCT No.: PCT/US2013/029524
§ 371 (c)(1),
(2) Date: Aug. 28, 2014

(87) PCT Pub. No.: WO2013/134468
PCT Pub. Date: Sep. 12, 2013

(65) Prior Publication Data
US 2015/0040756 A1    Feb. 12, 2015

Related U.S. Application Data

(60) Provisional application No. 61/607,924, filed on Mar. 7, 2012.

(51) Int. Cl.
*B01D 15/16* (2006.01)
*B01D 15/40* (2006.01)
(Continued)

(52) U.S. Cl.
CPC ......... *B01D 53/0454* (2013.01); *B01D 15/16* (2013.01); *B01D 15/163* (2013.01);
(Continued)

(58) Field of Classification Search
CPC ...... B01D 15/10; B01D 15/16; B01D 15/163; B01D 15/40; B01D 53/04; B01D 53/0454;
(Continued)

(56) References Cited

U.S. PATENT DOCUMENTS 3,788,352 A * 1/1974 Ane .................. F16K 47/10
137/513.5
4,744,387 A * 5/1988 Otteman ............ G05D 16/0661
137/505

(Continued)

OTHER PUBLICATIONS

Image Permanence Institute at Rochester Institute of Technology, "Dew Point Calculator". http://www.dpcalc.org/.*
(Continued)

*Primary Examiner* — Benjamin L Lebron
(74) *Attorney, Agent, or Firm* — Womble Bond Dickinson (US) LLP; Deborah M. Vernon; Heath T. Misley (57) ABSTRACT

Exemplary embodiments of the present disclosure include systems, apparatuses, and methods that are directed to controlling pressure in a pressurized flow system, such as a $CO_2$-based chromatography system or other pressurized flow systems. Exemplary embodiments of the present disclosure comprise one or more apparatuses, systems or methods for implementing multiple pressure regulators to control pressure. In addition to providing pressure control, apparatuses, systems and methods described herein dampen damaging thermal effects caused by pressure drops of a mobile phase including $CO_2$.

12 Claims, 9 Drawing Sheets

(51) Int. Cl.
  *B01D 53/04* (2006.01)
  *G01N 30/02* (2006.01)
  *G01N 30/32* (2006.01)
  *G01N 30/36* (2006.01)
  *G01N 30/30* (2006.01)
  *G05D 16/00* (2006.01)
  *B01D 15/10* (2006.01)

(52) U.S. Cl.
  CPC ............ *B01D 15/40* (2013.01); *B01D 53/04* (2013.01); *G01N 30/02* (2013.01); *G01N 30/36* (2013.01); *G05D 16/00* (2013.01); *G05D 16/024* (2019.01); *B01D 15/10* (2013.01); *G01N 30/32* (2013.01); *G01N 2030/3038* (2013.01); *G01N 2030/328* (2013.01)

(58) Field of Classification Search
  CPC ........ G01N 30/02; G01N 30/32; G01N 30/36; G01N 2030/3038; G01N 2030/328; G05D 16/00; G05D 16/024
  See application file for complete search history.

(56) References Cited

U.S. PATENT DOCUMENTS

| | | | |
|---|---|---|---|
| 4,984,602 A | 1/1991 | Saito et al. | |
| 5,224,510 A * | 7/1993 | Pericles | F16K 31/004 137/341 |
| 5,322,626 A | 6/1994 | Frank et al. | |
| 5,379,629 A | 1/1995 | Muller | |
| 5,439,027 A * | 8/1995 | Layton | F16K 1/385 137/513.5 |
| 5,653,884 A * | 8/1997 | Smart | B01D 11/0203 210/175 |
| 2003/0015019 A1 | 1/2003 | O'Brien | |
| 2011/0094606 A1* | 4/2011 | Kanomata | B01D 15/40 137/487.5 |

OTHER PUBLICATIONS

Strode, B., Thompson, J., Taylor, L., Anton, K., Bach, M., and Pericles, N. (1997). Packed Column Supercritical Fluid Chromatography—Evaporative Light-Scattering Detection. In Anton, K. and Berger, C. (Eds.), Supercritical Fluid Chromatography with Packed Columns: Techniques and Applications (pp. 103, 104, 122). New York: Marcel Dekker, Inc.*

Image Permanence Institute at Rochester Institute of Technology, "Dew Point Calculator". http://www.dpcalc.org/. Accessed Feb. 14, 2017.*

Guiochon G, et al., Fundamental challenges and opportunities for preparative supercritical fluid chromatography. J Chromatogr A. Feb. 25, 2011;1218(8):1037-114.

International Search Report for PCT/US2013/029524, dated May 13, 2013.

* cited by examiner

REGULATOR FOR IMPROVED THERMAL AND PRESSURE CONTROL FOR CHROMATOGRAPHY

RELATED APPLICATIONS

This application is a National Stage Application of International Application No. PCT/US2013/029524, filed Mar. 7, 2013, which claims priority to U.S. Provisional Application No. 61/607,924, filing date Mar. 7, 2012. Each of the foregoing applications is incorporated herein by reference in its entirety.

FIELD OF THE TECHNOLOGY

In general, the field of the technology of the present disclosure is directed to methods and related apparatus and systems for controlling pressure in a pressurized flow system, such as, for example, a $CO_2$-based chromatography system. In particular, the field of the technology is directed to methods and related apparatus and systems including a two stage pressure regulator (e.g., dynamic regulator followed by a static regulator) to control pressure.

BACKGROUND

Chromatographic techniques are important tools for the identification and separation of complex samples. The basic principle underlying chromatographic techniques is the separation of a mixture into individual components by transporting the mixture in a moving fluid through a retentive media. The moving fluid is typically referred to as the mobile phase and the retentive media is typically referred to as the stationary phase. The separation of the various constituents of the mixture is based on differential partitioning between the mobile and stationary phases. Differences in components' partition coefficient result in differential retention on the stationary phase, resulting in separation.

Conventionally, the methods of choice for chromatographic separations have been gas chromatography (GC) and liquid chromatography (LC). One major difference between GC and LC is that the mobile phase in GC is a gas, whereas the mobile phase in LC is a liquid. For example, in GC, a supply of inert carrier gas (mobile phase) is continually passed as a stream through a heated column containing porous sorptive media (stationary phase). A sample of the subject mixture is injected into the mobile phase stream and passed through the column, where separation of the mixture is primarily due to the differences in the volatile characteristics of each sample component at the temperature of the column. A detector, positioned at the outlet end of the column, detects each of the separated components as they exit the column. Although GC is typically a sensitive method of analysis, the high temperatures required in GC make this method unsuitable for high molecular weight biopolymers or proteins (heat will denature them), frequently encountered in biochemistry.

Conversely, LC is a separation technique in which the mobile phase is a liquid and does not require volatilization of the sample. Liquid chromatography that generally utilizes small packing particles and moderately high pressure is referred to as high-performance liquid chromatography (HPLC); whereas liquid chromatography that generally utilizes very small packing particles and high pressure is referred to as ultra-high performance liquid chromatography (UHPLC). In HPLC and UHPLC the sample is forced by a liquid at high pressure (the mobile phase) through a column that is packed with a stationary phase composed of irregularly or spherically shaped particles, a porous monolithic layer, or a porous membrane.

Because LC uses liquid as the mobile phase, LC techniques are capable of analyzing higher molecular weight compounds and, in some cases, LC can be used to prepare large scale batches of purified protein(s). However, in contrast, GC techniques are typically more sensitive and readily allow for the separation of single chiral materials. Thus, GC has conventionally been used to isolate and determine the relative purity of a chiral compound, e.g., by determining the enantiomeric excess (% ee) or the diastereomeric excess (% de) of a particular sample. As with most chromatographic techniques, the limiting factor in both GC and LC has been the ability to obtain and/or reproduce pure sample separations, each of which are typically dependent on the apparatus, methods, and conditions employed, e.g., flow rate, column size, column packing material, solvent gradient, etc.

Figure 1:
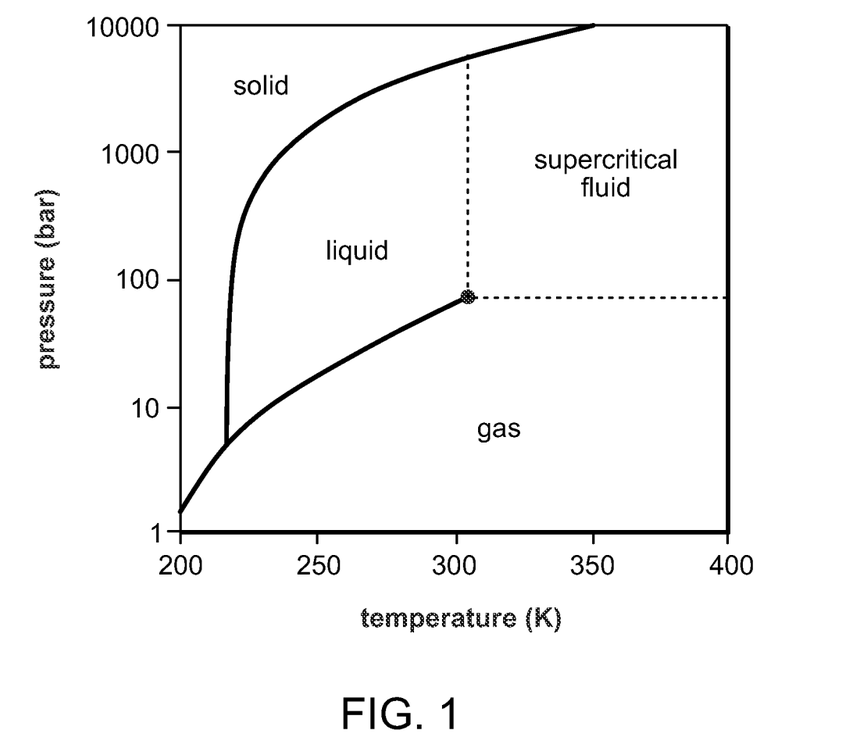
FIG. 1 is an exemplary graph of the physical state of a substance in relation to a temperature and pressure associated with the substance.

Supercritical Fluid Chromatography is another chromatographic technique, which has typically been used in preparative applications. For every liquid substance there is a temperature above which it can no longer exist as a liquid, no matter how much pressure is applied. Likewise, there is a pressure above which the substance can no longer exist as a gas no matter how much the temperature is raised. These points are called the supercritical temperature and supercritical pressure, and define the boundaries on a phase diagram for a pure substance (FIG. 1). At this point, the liquid and vapor have the same density and the fluid cannot be liquefied by increasing the pressure. Above this point, where no phase change occurs, the substance acts as a supercritical fluid (SF). Thus, SF can be described as a fluid obtained by heating above the critical temperature and compressing above the critical pressure. There is a continuous transition from liquid to SF by increasing temperature at constant pressure or from gas to SF by increasing pressure at constant temperature.

The term SFC, while typically standing for Supercritical Fluid Chromatography, does not require or mean that supercritical conditions are obtained during or maintained throughout the separation. That is, columns do not have to be always operated in the critical region of the mobile phase. For example, in the event that the mobile phase includes a modifier (e.g., $CO_2$ and methanol as a modifier), the mobile phase is often in its subcritical region (e.g., a highly compressed gas or a compressible liquid rather than a supercritical fluid). In fact, as Guiochon et al note in section 2.3 of their review article entitled "Fundamental challenges and opportunities for preparative supercritical fluid chromatography" Journal of Chromatography A, 1218 (2011) 1037-1114: "It is obvious that SFC has very often been and still is run under subcritical conditions." Thus, the term SFC is not limited to processes requiring supercritical conditions.

Because SFC typically uses $CO_2$, SFC processes are inexpensive, innocuous, eco-friendly, and non-toxic. There is typically no need for the use of volatile solvent(s) (e.g., hexane). Finally, the mobile phase in SFC processes (e.g., $CO_2$ together with any modifier/additive as a SF, highly compressed gas, or compressible liquid) typically have higher diffusion constants and lower viscosities relative to liquid solvents. The low viscosity means that pressure drops across the column for a given flow rate is greatly reduced. The increased diffusivity means longer column length can be used.

SUMMARY

Exemplary embodiments of the present disclosure include systems, apparatuses, and methods that are directed to controlling the pressure in a pressurized flow system, such as a $CO_2$-based chromatography system or other pressurized flow systems. Exemplary embodiments of the present disclosure include a two stage or combination regulator for controlling pressure. Methods, systems, and apparatuses described herein include the use of a dynamic pressure regulator followed by a static pressure regulator to control the phase and pressure of a mobile phase media. For example, embodiments include setting the static pressure regulator inlet pressure to a pressure above the critical pressure for the mobile phase media. As a result, the mobile phase media passing through the dynamic pressure regulator is maintained in the liquid phase. In general, a pressure regulator, such as a dynamic pressure regulator, can better (e.g., more consistently) control pressure of a single phase (e.g., liquid phase) material across its inlet and outlet. In addition, embodiments include controlling the phase change of the mobile phase media within the static pressure regulator and heating at least a portion of the static pressure regulator to prevent or minimize freezing and its effects on the static pressure regulator. Systems, apparatus and methods described herein can dampen damaging effects caused by pressure drops of a supercritical fluid, while providing accurate pressure control.

In one embodiment, a method for controlling the pressure of a mobile phase in a pressurized flow system is disclosed. The method includes, for example, pre-heating and/or post-heating the mobile phase to eliminate issues related to, e.g., condensation, frost, clogging and sputtering, and pressure disturbances and fluctuations throughout the pressurized flow system. Systems and apparatuses for controlling the pressure are also disclosed.

In accordance with embodiments of the present technology, methods for controlling pressure of a mobile phase in a pressurized flow system include the following steps: passing a mobile phase into a first regulator (e.g., a dynamic pressure regulator) in a first phase state; varying the pressure inside the first regulator while maintaining the first phase state; passing the mobile phase into a second regulator (e.g., a static pressure regulator); causing the first phase state to change to a second phase state different from the first phase state in the second regulator; heating an element: before the second regulator (but after the first regulator), within the second regulator, or after the second regulator, or a combination of heating thereof, to a temperature sufficient to keep said mobile phase above a temperature of about 0° C. (e.g., ambient temperature); and passing the mobile phase through the element.

Embodiments of the above exemplary method can include one or more of the following features. In embodiments, heating the element occurs before the second regulator or within the second regulator or a combination thereof. In embodiments, the pressurized flow system is a chromatographic system, such as, for example, a $CO_2$-based chromatography system. That is, the mobile phase includes carbon dioxide (e.g., 100% carbon dioxide, 90% carbon dioxide and 10% modifier/additive/etc., a gradient composition including carbon dioxide). In some embodiments, the first phase state is a supercritical phase state. In other embodiments, the first phase state is a liquid phase state. In embodiments, the second phase state is a gas phase state. In some embodiments of the above method, the element is heated to the internal temperature that keeps the mobile phase at a temperature above the dew point temperature of the system to substantially eliminate condensation on the system (e.g., at or near the second regulator). Any combination or permutation of embodiments is envisioned.

In accordance with embodiments of the present technology, an apparatus for controlling pressure of a mobile phase in a pressurized flow system is disclosed. The apparatus includes a first pressure regulator with an actuator to control pressure output (e.g., a dynamic pressure regulator); a second pressure regulator with an internal surface that allows for a pressure drop of a mobile phase substance (e.g., a static pressure regulator); and a heating element positioned: before the second pressure regulator, within the second pressure regulator, or after the second pressure regulator, or a combination thereof, such that the heating element is configured in a manner to maintain the mobile phase above a temperature of about 0° C. (e.g., at ambient temperature).

Embodiments of the above exemplary apparatus can include one or more of the following features. In some embodiments, the apparatus includes a second heating element in connection with the second pressure regulator. In certain embodiments, the heating element is configured to maintain the mobile phase at or above the dew point temperature of the chromatographic system (i.e., at the location of the chromatographic system). As a result of heating the mobile phase at or above the dew point temperature, condensation on the exterior of the chromatographic system is substantially reduced or eliminated, especially at or near the location of the second pressure regulator. In embodiments, the chromatographic system is a $CO_2$-based chromatographic system. Any combination or permutation of embodiments is envisioned.

The exemplary systems, methods, and apparatuses of the present disclosure provide numerous advantages. For example, the systems, methods, and apparatuses can control pressure while minimizing damaging effects of phase changes and pressure drops in a $CO_2$-based chromatographic system. In general, the inlet to the static pressure regulator can be set at a pressure above the critical pressure for the mobile phase material, thereby guaranteeing that the mobile phase material is in a liquid phase through the dynamic pressure regulator. As a result of being a liquid phase throughout its flow path within the dynamic pressure regulator, pressure can be consistently controlled. Changes in phase can cause the mobile phase to gasify upstream of the regulator causing pressure consistency problems. Thus, by forcing the phase of the mobile phase media to remain as a liquid throughout the dynamic pressure regulator, improvements in pressure control consistency can be achieved.

Another advantage provided by embodiments of the present technology includes a reduction in damaging effects caused by pressure drops of a $CO_2$ fluid at or near supercritical conditions. For example, by restricting the phase change of the mobile phase media to occur in the static pressure regulator, one can localize the effects of the phase change. In general, the phase change of $CO_2$ from a liquid to a supercritical fluid is endothermic, and thus the phase change location needs to be heated to prevent freezing. By controlling the location of the phase change (e.g., restricting phase change to the static pressure regulator), heating can be simplified and localized to this particular location (e.g., static pressure regulator). In addition, in the event that the localized heating does not prevent all damage, the damage is limited to the static pressure regulator. As a result, only the static pressure regulator component, and not the dynamic pressure regulator, would be repaired or replaced.

BRIEF DESCRIPTION OF THE DRAWINGS

The foregoing and other features and advantages provided by the present disclosure will be more fully understood from the following description of exemplary embodiments when read together with the accompanying drawings, in which:

FIG. 8 represents a pressure regulator heating system according to an embodiment of the present disclosure, where a) illustrates a heating element and a static pressure regulator, and b) illustrates the system with the static pressure regulator removed.

DETAILED DESCRIPTION

SFC can be adapted as a hybrid between HPLC and GC apparatuses, where the predominant modification is replacement of either the liquid or gas mobile phase with a supercritical fluid (or near supercritical fluid) mobile phase, such as with $CO_2$. In SFC, the mobile phase is initially pumped as a liquid or gas and is brought into the supercritical region by heating or pressurizing the mobile phase above its supercritical temperature/pressure prior to entry into a column. As the mobile phase passes through an injection valve, the sample is introduced into the supercritical stream, and the mixture is then transferred into a column. The mixture passes through the column (at supercritical or liquid state) and into the detector.

In general, the mobile phase in SFC processes have the ability to act both as substance carriers (like the mobile phases in GC), and dissolve substances readily (like the solvents used in LC). In addition to generally having lower viscosities and better diffusion profiles similar to those of certain gases, the mobile phase in SFC processes also generally have high densities and dissolving capacities similar to those of certain liquids. For example, SFs' high densities (0.2-0.5 $gm/cm^3$) provide for their remarkable ability to dissolve large, non-volatile molecules, e.g., supercritical or near supercritical $CO_2$ readily dissolves n-alkanes, di-n-alkyl phthalates, and polycyclic and aromatic compounds. Since the diffusion of solutes in a SFC mobile phase is about ten times greater than that in liquids (about three times less than in gases), this results in a decrease in resistance to mass transfer in the column and allows for fast high resolution separation. Also, the solvation strength of the mobile phase in SFC processes is directly related to the fluid density. Thus, the solubility of solids can be easily manipulated by making slight changes in temperatures and pressures.

Another important property of the mobile phase in SFC processes is that it provides high resolution chromatography at much lower temperatures. For example, an analyte dissolved in supercritical $CO_2$ can be recovered by reducing the pressure and allowing the sample to evaporate under ambient laboratory conditions. This property is useful when dealing with thermally unstable analytes, such as high molecular weight biopolymers or proteins.

The combination of one or more mechanical or column changes to an SFC instrument (e.g., a $CO_2$-based chromatography instrument) coupled with the inherent properties of the SFC itself, allows for the separation of both chiral and achiral compounds, and has become increasingly predominant in the field of preparatory separations for drug discovery and development. Despite considerable advances in SFC technology, there is a need to develop innovative methods and apparatuses that improve the use of SFC. Controlling and stabilizing the pressure in an SFC instrument by one or more process and/or improving one or more of the instrumental characteristics of the system, may lead to, amongst others, improved compound separation and efficiency.

For example, better resolution and increased flow rate would decrease cycle times (i.e., shorter cycle times) and allow for improved separation of both chiral and achiral compounds, and lead to an overall increase in laboratory efficiency; increased speed and throughput would decrease the amount of solvent and cost(s) associated with SFC; and the ability to further integrate SFC with other detection methods, such as Mass Spectrometry (MS), Flame Ionization Detectors (FID), and Ultraviolet/Visible (UV) detectors, would improve the mainstream use of SFC using a mobile phase including $CO_2$ as an eco-friendly, yet effective, alternative method for the fast, complete, and sensitive analysis of analytes.

Exemplary embodiments of the present disclosure are directed to improved thermal and pressure control in a pressurized flow system, such as, for example a $CO_2$-based chromatography system. Exemplary embodiments can implement one or more systems, apparatus and/or methods utilizing a two stage pressure regulator. In embodiments, the two stage pressure regulator includes a dynamic regulator upstream of a heated static pressure regulator. In general, an inlet pressure to the static pressure regulator is set to a pressure above the critical pressure of the mobile phase media passing therethrough (e.g., $CO_2$). By incorporating a two stage regulator with a heated static regulator having a set inlet pressure higher than the critical pressure, the location of a phase change of the mobile phase media is restricted to occur within the static pressure regulator. As a result, the dynamic pressure regulator interacts only with a liquid phase material allowing for consistent pressure control. In addition, only the static regulator is exposed to low temperature (e.g., freezing) conditions. Accordingly, heating can be localized to the static pressure regulator to prevent or minimize damaging effects of freezing. In the event that heating fails to prevent all thermal damage, only the static pressure regulator component needs to be repaired or replaced as the dynamic pressure regulator is shielded from the temperature drop (i.e., the phase change occurs downstream of the dynamic pressure regulator in the static pressure regulator).

As used herein, the terms "downstream" and "upstream" refer to relative locations in a system flow, wherein upstream refers to being associated with an earlier portion of the system flow compared to a later portion of the system flow and downstream refers to being associated with a later portion of the system flow compared to an earlier portion of the system flow.

Figure 2:
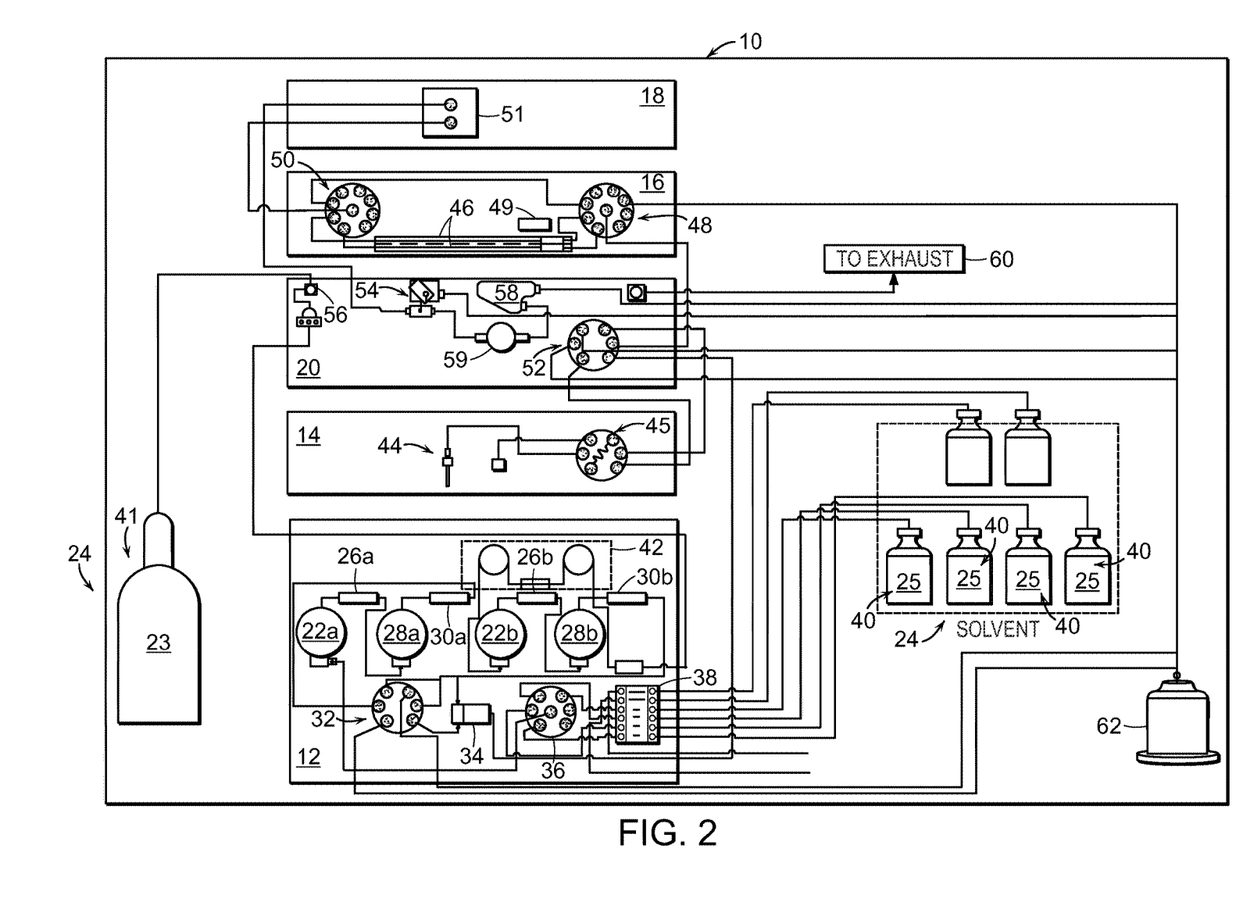
FIG. 2 is a block diagram of an exemplary pressurized flow system.

FIG. 2 is a block diagram of an exemplary pressurized flow system, which in the present embodiment is implemented as a $CO_2$-based chromatography system 10 (hereinafter "system 10"). While the present embodiment is illustrative of a $CO_2$-based chromatography system operated at or near supercritical conditions, those skilled in the art will recognize that exemplary embodiments of the present disclosure can be implemented as other pressurized flow systems and that one or more system components of the present disclosure can be implemented as components of other pressurized systems. System 10 can be configured to detect sample components of a sample using chromatographic separation in which the sample is introduced into a mobile phase that is passed through a stationary phase. System 10 can include one or more system components for managing and/or facilitating control of the physical state of the mobile phase, control of the pressure of system 10, introduction of the sample to the mobile phase, separation of the sample into components, and/or detection of the sample components, as well as venting of the sample and/or mobile phase from system 10.

Figure 3:
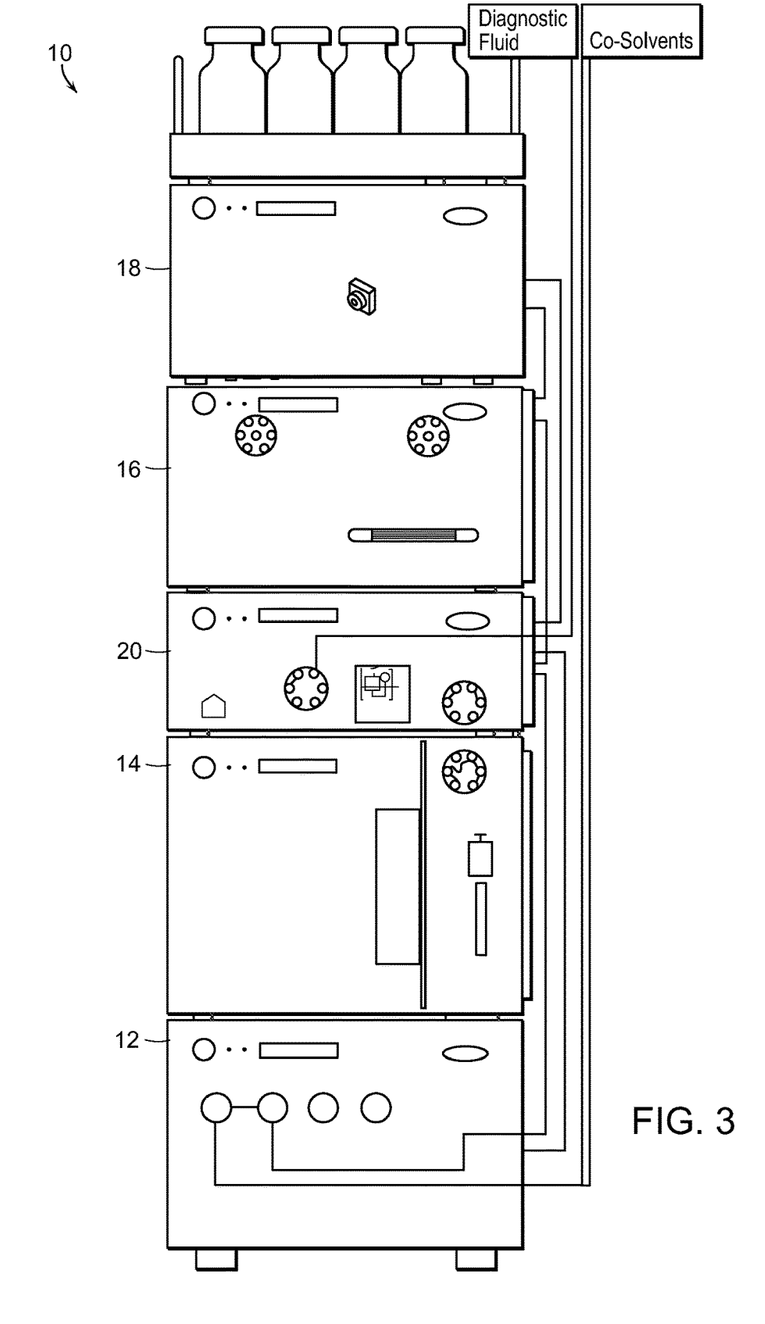
FIG. 3 is a block diagram of an exemplary arrangement of an embodiment of the system of FIG. 2.
Figure 4:
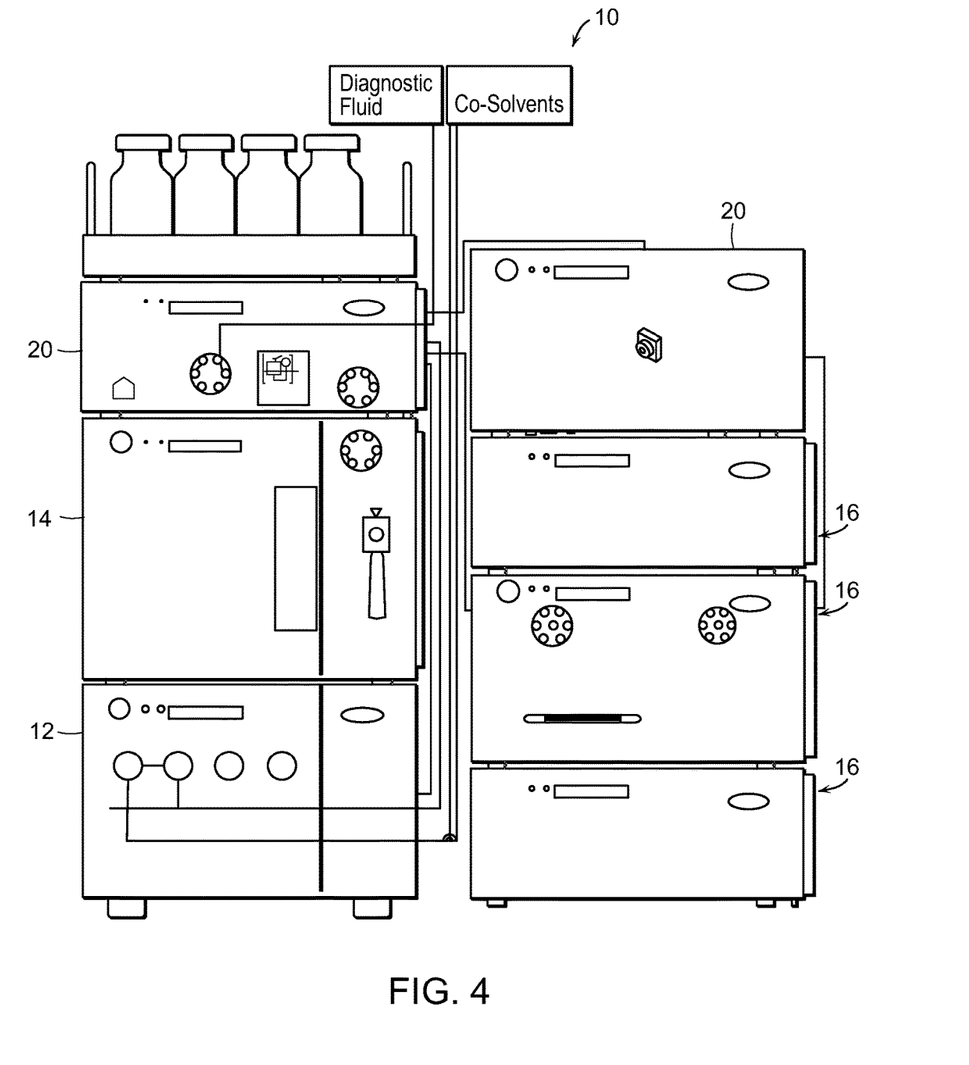
FIG. 4 is a block diagram of another exemplary arrangement of an embodiment of the system of FIG. 2.

In the present embodiment, system 10 can include a solvent delivery system 12, a sample delivery system 14, a sample separation system 16, a detection system 18 (e.g., a PDA detector), and system/convergence manager 20. In some embodiments, the system components can be arranged in one or more stacks. As one example, in one embodiment, the system components of system 10 can be arranged in a single vertical stack (FIG. 3). As another example, the system components of system 10 can be arranged in multiple stacks (FIG. 4). Those skilled in the art will recognize that other arrangements of the components of system 10 are possible. Furthermore, while embodiments of system 10 have been illustrated as including system components 12, 14, 16, 18, and 20, those skilled in the art will recognize that embodiments of the system 10 can be implemented as a single integral unit, that one or more components can be combined, and/or that other configurations are possible.

The solvent delivery system 12 can include one or more pumps 22a, 22b configured to pump one or more solvents 24, such as mobile phase media 23 (e.g., carbon dioxide) and/or modifier media 25 (i.e., a co-solvent, such as, e.g., methanol, ethanol, 2-methoxyethanol, isopropyl alcohol, or dioxane), through system 10 at a predetermined flow rate. For example, the pump 22a can be in pumping communication with the modifier media 25 to pump the modifier media 25 through system 10, and the pump 22b can be in pumping communication with the mobile phase media 23 to pump the mobile phase media 23 through system 10. An output of the pump 22a can be monitored by a transducer 26a and an output of the pump 22b can be monitored by a transducer 26b. The transducers 26a, 26b can be configured to sense the pressure and/or flow rate associated with the output of the solvent 24 from the pumps 22a, 22b, respectively.

The outputs of the pumps 22a, 22b can be operatively coupled to an input of accumulators 28a and 28b, respectively. The accumulators 28a and 28b are refilled by the outputs of the pumps 22a and 22b, respectively, and can contain an algorithm to reduce undesired fluctuations in the flow rate and/or pressure downstream of the pumps 22a and 22b, which can cause detection noise and/or analysis errors on the system 10. An output of the accumulator 28a can be monitored by a transducer 30a and an output of the accumulator 28b can be monitored by a transducer 30b. The transducers 30a, 30b can be configured to sense pressure and/or flow rate at an output of the accumulators 28a, 28b, respectively. The outputs of the accumulators 28a, 28b can be operatively coupled to a multiport valve 32, which can be controlled to vent the solvent 24 (e.g., mobile phase media 23 and modifier media 25) being pumped by the pumps 22a, 22b and/or to output the solvent 24 to a mixer 34. The mixer 34 can mix the modifier media 25 and the mobile phase media 23 output from the pumps 22a, 22b, respectively (e.g., after first passing through the accumulators 28a, 28b) and can output a mixture of the mobile phase media 23 and the modifier media 25 to form a solvent stream (i.e., mobile phase) that flows through the system 10. The output of the mixer 34 can be operatively coupled to the system/convergence manager 20 as discussed in more detail below.

In exemplary embodiments, the solvent delivery system 12 can include a multiport solvent selection valve 36 and/or a degasser 38. The solvent selection valve 36 and/or the degasser 38 can be operatively disposed between an input of the pump 22a and solvent sources, e.g., solvent containers 40, such that the solvent selection valve 36 and/or the degasser 38 are positioned upstream of the pump 22a. The solvent selection valve 36 can be controlled to select the modifier media 23 to be used by the system 10 from one or more solvent containers 40 and the degasser 38 can be configured to remove dissolved gases from the media modifier 23 before the media modifier 23 is pumped through the system 10.

In exemplary embodiments, the solvent delivery system 12 can include a pre-chiller 42 disposed between an input of the pump 22b and a solvent source, e.g., solvent container 41, such that the pre-chiller is disposed upstream of the input to the pump 22b and downstream of the solvent container 41. The pre-chiller 42 can reduced the temperature of the mobile phase media 23 before it is pumped through the system 10 via the pump 22b. In the present embodiment, the mobile phase media 23 can be carbon dioxide. The pre-chiller can decrease the temperature of the carbon dioxide so that the carbon dioxide is maintained in a liquid state (i.e., not a gaseous state) as it is pumped through at least a portion of the system 10. Maintaining the carbon dioxide in a liquid state can facilitate effective metering of the carbon dioxide through the system 10 at the specified flow rate.

The pumps 22a, 22b can pump the solvent 24 through the system 10 to pressurize system 10 to a specified pressure, which may be controlled, at least in part, by the system/convergence manager 20. In exemplary embodiments, the system 10 can be pressurized to a pressure between about 700 psi and about 18,000 psi or about 1,400 psi and about 8,000 psi. In one embodiment, the system 10 can be pressurized to a pressure of about 6,000 psi. By pressurizing the system 10 at these pressure levels (such as those pressure levels described above), the solvent stream (i.e., mobile phase) can be maintained in a liquid state before transitioning to a supercritical fluid state or near supercritical state (e.g., highly compressed gas or compressible liquid) for a chromatographic separation in a column, which can be accomplished by raising the temperature of the pressurized solvent stream.

The sample delivery system 14 can select one or more samples to be passed through the system 10 for chromatographic separation and detection. The sample delivery system 14 can include a sample selection and injection member 44 and a multi-port valve 45. The sample selection and injection member 44 can include a needle through which the sample can be injected into the system 10. The multiport valve 45 can be configured to operatively couple the sample selection and injection member 44 to an input port of the system/convergence manager 20.

The sample separation system 16 can receive the sample to be separated and detected from the sample delivery system 14, as well as the pressurized solvent stream from the solvent delivery system 12, and can separate components of the sample passing through the system 10 to facilitate detection of the samples using the detection system 18. The sample separation system 16 can include one or more columns 46 disposed between an inlet valve 48 and an outlet valve 50. The one or more columns 46 can have a generally cylindrical shape that forms a cavity, although one skilled in the art will recognize that other shapes and configurations of the one or more columns is possible. The cavity of the columns 46 can have a volume that can at least partially be filled with retentive media, such as hydrolyzed silica, such as $C_8$ or $C_{18}$, or any hydrocarbon, to form the stationary phase of the system 10 and to promote separation of the components of the sample. The inlet valve 48 can be disposed upstream of the one or more columns can be configured to select which of the one or more columns 46, if any, receives the sample. The outlet valve 50 can be disposed downstream of the one or more columns 46 to selective receive an output from the one or more columns 46 and to pass the output of the selected one or more columns 46 to the detection system 18. The columns 46 can be removeably disposed between the valves 48, 50 to facilitated replacement of the one or more columns 46 new columns after use. In some embodiments, multiple sample separation systems 16 can be included in the system 10 to provide an expanded quantity of columns 46 available for use by the system 10 (FIG. 4).

In exemplary embodiments, the sample separation system 16 can include a heater 49 to heat the pressurized solvent stream 24 prior and/or while the pressured solvent stream 24 passes through the one or more columns 46. The heater 49 can heat the pressurized solvent stream to a temperature at which the pressured solvent transition from a liquid state to a supercritical fluid state so that the pressurized solvent stream passes through the one or more columns 46 as a supercritical fluid.

Referring again to FIG. 2, the detection system 18 can be configured to receive components separated from a sample by the one or more columns 46 and to detect a composition of the components for subsequent analysis. In an exemplary embodiment the detection system 18 can include one or more detectors 51 configured to sense one of more characteristics of the sample components. For example, in one embodiment, the detectors 51 can be implemented as one or more photodiode arrays.

The system/convergence manager 20 can be configure to introduce a sample from the sample delivery system 14 into the pressurized solvent stream flowing from the solvent delivery system 12 and to pass the solvent stream and sample to the sample separation system 16. In the present embodiment, the system/convergence manager 20 can include a multiport auxiliary valve 52 which receives the sample injected by the sample delivery system 14 through a first inlet port and the pressurized solvent stream from the solvent delivery system 12 through a second inlet port. The auxiliary valve 52 can mix the sample and the solvent stream and output the sample and solvent stream via an outlet port of the multiport auxiliary valve 52 to an inlet port of the inlet valve 48 of the sample separation system 16.

The system/convergence manager 20 can also be configured to control the pressure of the system 10 and to facilitate cooling, heating and/or venting of the solvent from system 10, and can include a vent valve 54, a shut off valve 56, a back pressure regulator 58, and a transducer 59. The vent valve 54 can be disposed downstream of the detection system 18 can be configured to decompress the system 10 by venting the solvent from the system 10 after the solvent has passed through the system 10. The shut off valve 56 can be configured to disconnect the solvent supply from the inlet of the pump 22b of the solvent delivery system to prevent the solvent from being pumped through the system 10.

The back pressure regulator 58 can control the back pressure of the $CO_2$-based chromatography system 10 to control the flow of the mobile phase and sample through the column, to maintain the mobile phase in the supercritical fluid state (or, in some embodiments, in a near supercritical state, such as a highly-compressed gas or compressible liquid) as the mobile phase passes through the one or more columns 46 of the sample separation system 16, and/or to prevent the back pressure from forcing the mobile phase reversing its direction a flow through the one or more columns 46. Embodiments of the back pressure regulator 58 can be configured to regulate the pressure of the system 10 so that the physical state of the solvent stream (i.e., mobile phase) does not change uncontrollably upstream of and/or within the back pressure regulator 58. The transducer 59 can be a pressure sensor disposed upstream of the back pressure regulator 58 to sense a pressure of the system 10. The transducer 59 can output a feedback signal to a processing device which can process the signal to control an output of an actuator control signal from the processing device.

Figure 5:
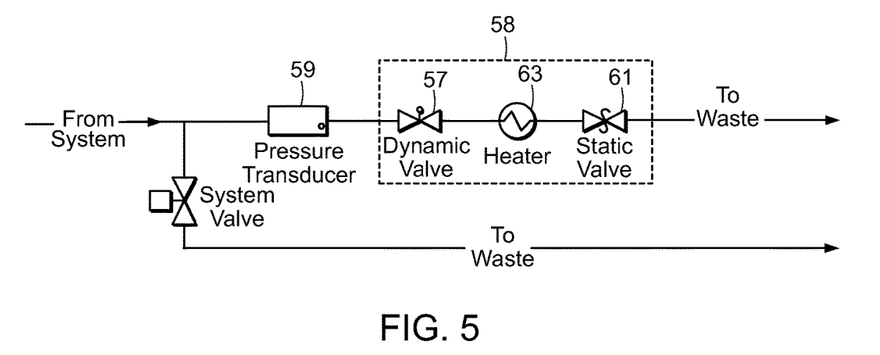
FIG. 5 is a flow diagram of a mobile phase through a system manager portion of the an exemplary embodiment of the pressurized flow system.

In exemplary embodiments, as shown in FIG. 5, the back pressure regulator 58 can include a dynamic pressure regulator 57, a static pressure regulator 61, and a heater 63. The static pressure regulator 61 can be configured to maintain a predetermined pressure upstream of the back pressure regulator 58. The dynamic pressure regulator 57 can be disposed upstream of the static pressure regulator 61 and can be configured to set the system pressure above the predetermined pressure maintained by the static regulator 61. The heater 63 can be disposed downstream of the dynamic pressure regulator 57 and can be disposed in close proximity to the static pressure regulator 61 to heat the solvent stream as it passes through the static pressure regulator 61 to aid in control of the physical state of the solvent as it passes through the static pressure regulator. The structure, function, and/or operation of the back pressure regulator 58, static pressure regulator, and/or dynamic regulator are described in more detail below.

In summary, an exemplary operation of the $CO_2$-based chromatography system 10 can pump mobile phase media 23 and modifier media 25 at a specified flow rate through the system 10 as a solvent stream (i.e., mobile phase) and can pressurize the system 10 to a specified pressure so that the solvent stream maintains a liquid state before entering the sample separation system 16. A sample can be injected into the pressurized solvent stream by the sample delivery system 14, and the sample being carried by the pressurized solvent stream can pass through the sample separation system 16, which can heat the pressurized solvent stream to transition the pressurized solvent stream from a liquid state to a supercritical fluid state. The sample and the supercritical fluid solvent stream can pass through at least one of the one or more columns 46 in the sample separation system 16 and the column(s) 46 can separate components of the sample from each other. The separated components can pass the separated components to the detection system 18, which can detect one or more characteristics of the sample for subsequent analysis. After the separated sample and solvent pass through the detection system 18, the solvent and the sample can be vented from the system 10 by the system/convergence manager 20.

In other embodiments, the system 10 described herein can also be used for preparatory methods and separations. Typical parameters, such as those described above, may be manipulated to achieve effective preparatory separations. For example, the system 10 described herein confers the benefit of exerting higher flow rates, larger columns, and column packing size, each of which contributes to achieving preparatory separation and function, while maintaining little or no variability in overall peak shape, peak size, and/or retention time(s) when compared to respective analytical methods and separations thereof. Thus, in one embodiment, the present disclosure provides $CO_2$-based chromatography systems, which are amendable to preparatory methods and separations with high efficiency and correlation to analytical runs.

Figure 6:
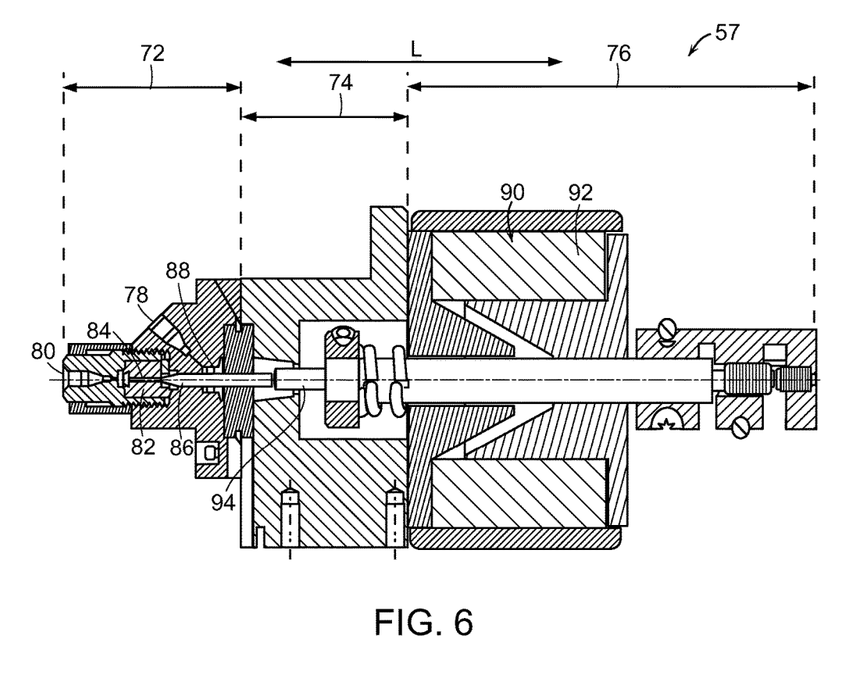
FIG. 6 is a cross-sectional view of a valve assembly for an exemplary dynamic pressure regulator in an exemplary embodiment of the pressurized system.

FIG. 6 is a cross-sectional view of an exemplary embodiment of a dynamic pressure regulator 57 along a longitudinal axis L of the dynamic pressure regulator. The dynamic pressure regulator 57 can be implemented as a valve assembly that includes a proximal head portion 72, an intermediate body portion 74, and a distal actuator portion 76. The head portion 72 of the valve assembly can include an inlet 78 to receive the pressurized solvent stream and an outlet 80 through which the pressurized solvent stream is output such that the solvent stream flows through the head portion from the inlet 78 to the outlet 80. A seat 82 can be disposed within the head portion 72 and can include a bore 84 through which the solvent stream can flow from the inlet 78 to the outlet 80 of the head.

A needle 86 extends into the head portion 72 from the body portion 74 of the valve assembly through a seal 88. A position of the needle 86 can be controlled with respect to the seat 82 to selectively control a flow of the solvent stream from the inlet 78 to the outlet 80. In exemplary embodiments, the position of the needle 86 can be used to restrict the flow through the bore 84 of the seat 82 to increase the pressure of the system 10 and can selectively close the valve by fully engaging the seat 82 to interrupt the flow between the inlet 78 and the outlet 80. By controlling the flow of the solvent stream through the head portion based on the position of the needle 86, the pressure of the system 10 can be increase or decreased. For example, the pressure of the system 10 can generally increase as the needle 86 moves towards the seat 82 along the longitudinal axis L and can generally decrease as the needle 86 moves away from the seat 82 along the longitudinal axis L.

The actuator portion 76 can include an actuator 90, such as a solenoid, voice coil, and/or any other suitable electromechanical actuation device. In the present embodiment, the actuator 90 can be implemented using a solenoid having a main body 92 and a shaft 94. The shaft 94 can extend along the longitudinal axis L and can engage a distal end of the needle 86 such that the needle 86 and shaft can form a valve member. A position of the shaft 94 can be adjustable with respect to the main body 92 along the longitudinal axis L and can be controlled by a coil (not shown) of the main body 92, which generates a magnetic field that is proportional to an electric current passing through the coil and a load applied to the shaft. The electric current passing through the coil can be controlled in response to an actuator control signal received by the actuator 90. In some embodiments, the actuator control signal can be a pulse width modulated (PWM) signal and/or the actuator control signal can be determined, at least in part, by the feedback signal of the pressure transducer 59.

The position of the shaft 94 can be used to move the needle 86 towards or away from the seat 82 to increase or decrease pressure, respectively. In exemplary embodiments, a position of the shaft 94, and therefore a position of the needle 86 with respect to the seat 82 can be controlled and/or determined based on an amount of electric current flowing through the solenoid. For example, the greater the electrical current the closer the needle 86 and shaft 94 are from the seat and the lower the pressure is in the system 10. The relationship between a position of the shaft 94 and the electric current flowing through the coil can be established through characterization of the actuator 90. The force imposed by the load on the solenoid can be proportional to the magnetic field. Similarly, the magnetic field can be proportional to the electric current flowing through the coil of the solenoid. For embodiments in which the actuator control signal is implemented as a PWM control signal, the pressure through the pressure regulator 57 (e.g., force balance between needle 86 and shaft 94) can be set by a correlation to the duty cycle of the PWM control signal, e.g., a percentage of the duty cycle corresponding to an "on" state.

Figure 7:
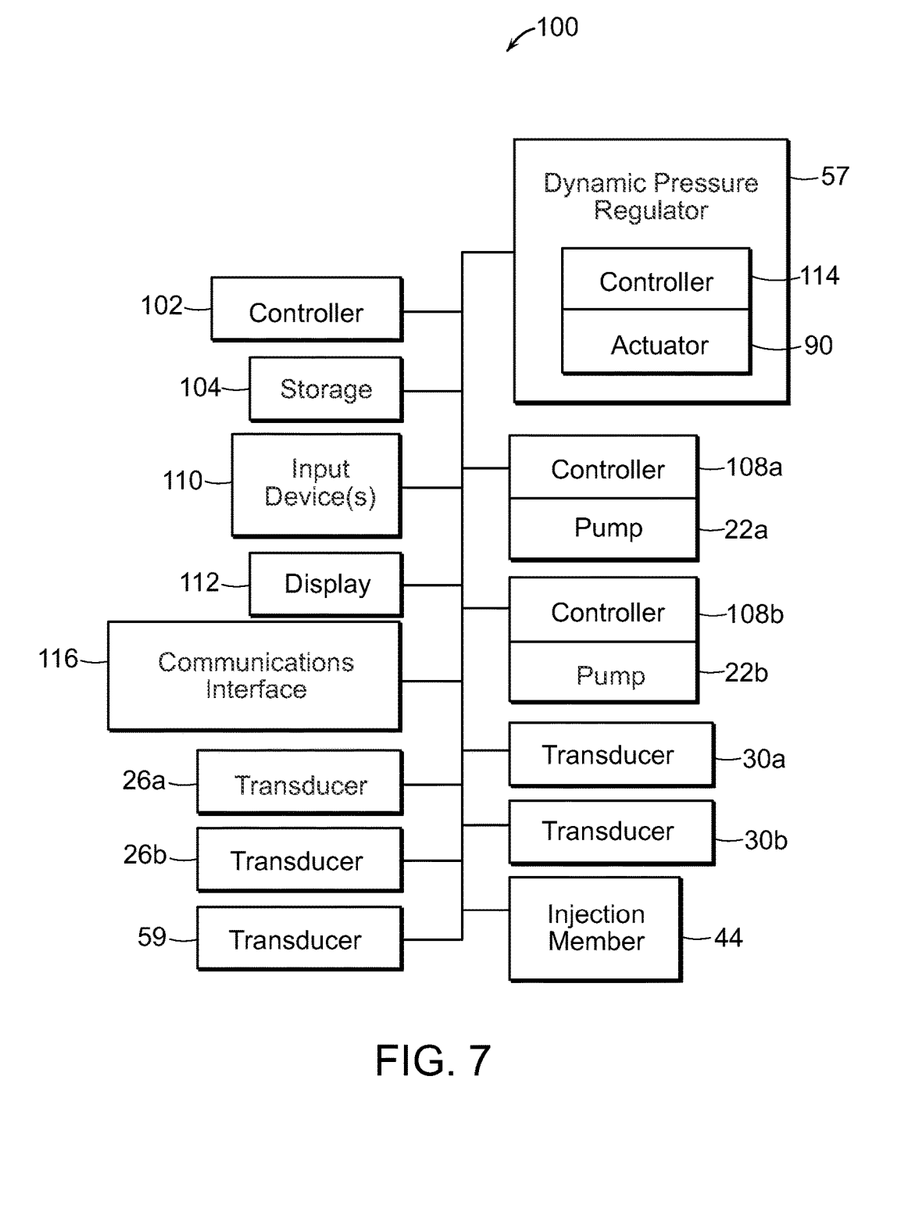
FIG. 7 is a block diagram of an exemplary control system that can be implemented to control an operation of an exemplary embodiment of the pressurized flow system.

FIG. 7 is a block diagram of an exemplary control system 100 that can be implemented to control the pressure of the system 10. The control system 100 can include a controller 102 in electrical communication with a storage device 104 (e.g., memory and/or other computer-readable storage mediums). The controller 102 can be implemented as a microcontroller, microprocessor, field programmable gate array (FPGA), and/or other processing devices. The storage 104 can be implemented as non-transitory computer readable medium including, for example, magnetic storage disks, optical disks, flash or solid state storage, and/or any other nonvolatile or volatile storage medium including random access memory, such as DRAM, SRAM, EDO RAM, MRAM, and the like. The storage 106 can store information corresponding to the system and/or components thereof. The storage 106 can also store instructions that are executable by the controller 102 to control an operation of system 10 including an operation of the dynamic back pressure regulator 57. The controller 102 can also be in communication with one or more of the pumps 22a, 22b, one or more of the transducers 26a, 26b, 30a, 30b, 59, the injection member 44, the dynamic pressure regulator 57, input devices 110, and/or a display 112. In this embodiment, the pumps, 22a, 22b can be associated with pump controllers 108a, 108b, respectively, and the actuator 90 of the dynamic pressure regulator 57 can be associated with an actuator controller 114.

The controller 102 can receive signals from and/or transmit signals to the transducers 26a, 26b, 30a, 30b, 59, the injection member 44, the pump controllers 108a, 108b, one or more input devices 110, such as a keyboard, mouse, or other suitable input devices, the display 112, and the actuator controller 114, and/or other devices, such as other controllers (e.g., processing devices), computing devices (e.g., a Laptop, PC, mainframe), networked devices (e.g., servers, databases), and the like, which can be communicatively coupled to the controller 102 via, for example, a communication interface 116. In exemplary embodiments, the controller 102 can process the received signals and can control an operation of the pumps 22a, 22b, the injection member 44, and/or the actuator 90 in response to the signals.

Figure 8A:
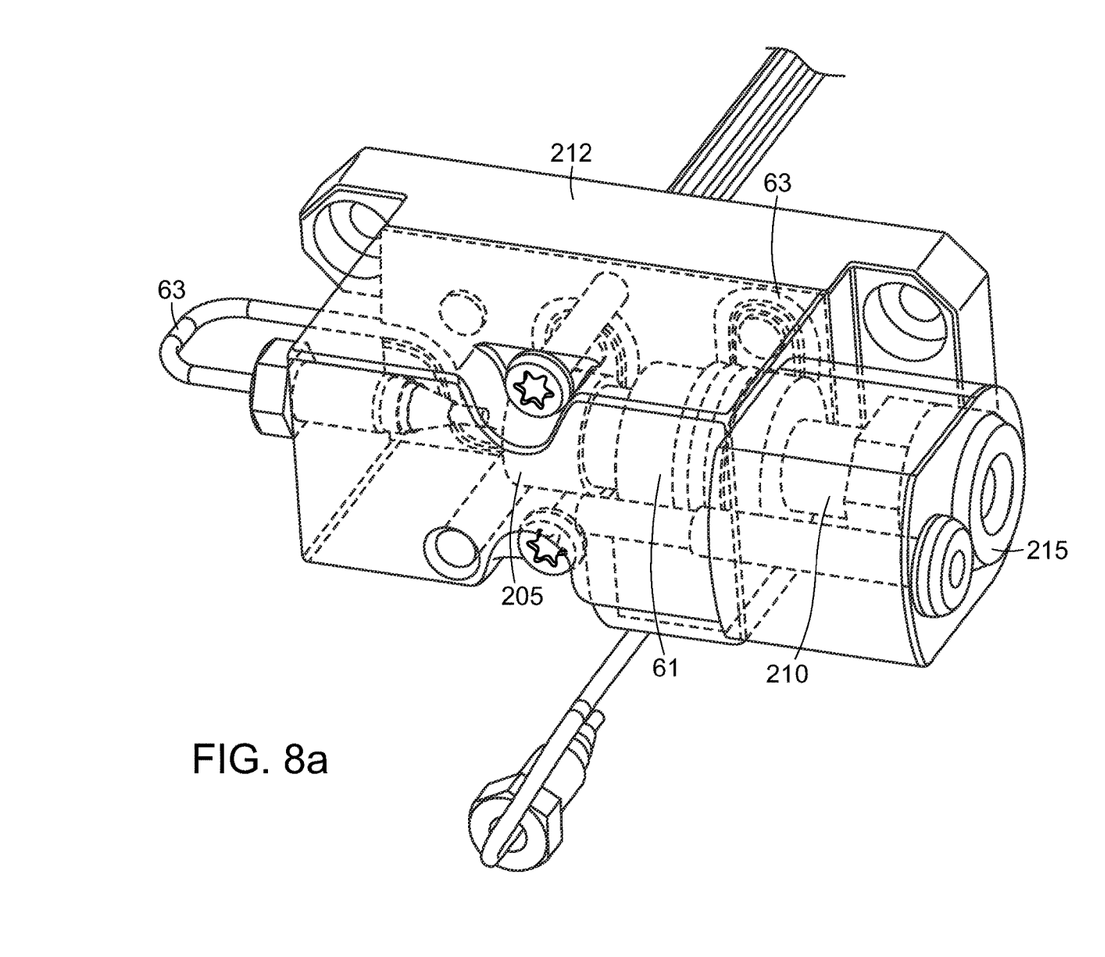
Figure 8B:
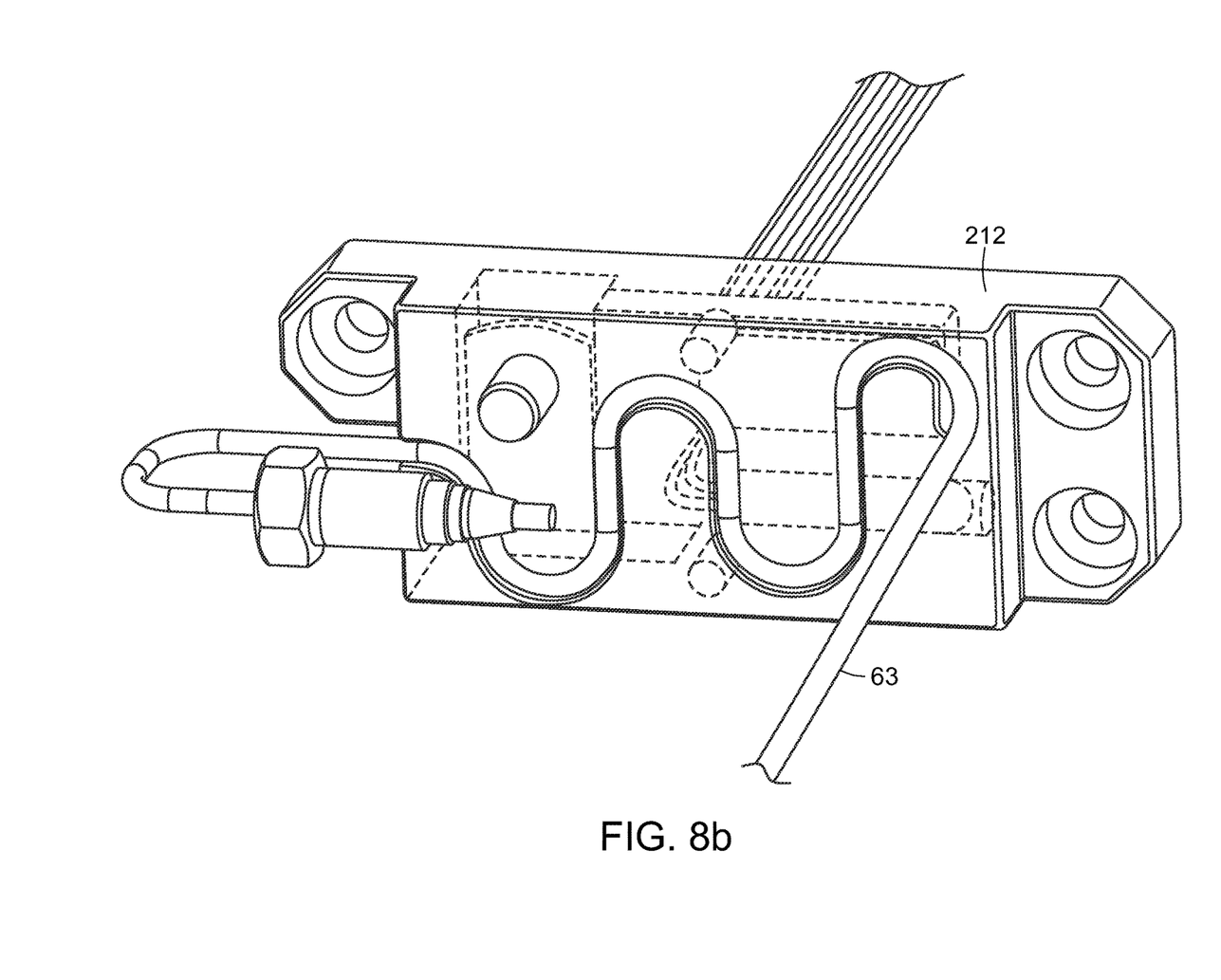

While the pressure through the dynamic pressure regulator 57 is controllable, the pressure across the static pressure regulator 61 is set. Referring to FIG. 5, to control pressure and thermal conditions of the mobile phase media, system 10 uses a two stage pressure regulator including the dynamic pressure regulator 57 and the static pressure regulator 61. The dynamic pressure regulator 57 is located upstream of the static pressure regulator 61 and positioned between regulator 57 and 61 is a heating element 63. In some embodiments, the heating element 63 is disposed between regulators 57 and 61 as shown in FIG. 5. In other embodiments, the heating element 63 is positioned not only between regulators 57 and 61, but also in physical contact with at least a portion of regulator 61. For example, FIGS. 8a and 8b illustrate an embodiment in which the heating element 63 extends from a location prior to (e.g., upstream of) a first end 205 of static regulator 61 and continues along a body 210 of the static regulator 61. In the embodiment shown in FIGS. 8a and 8b (FIG. 8b showing a similar view to that of FIG. 8a, but with the static pressure regulator 61 removed), heating element 63 is a coil or serpentine tube which is heated to a temperature sufficient to keep the mobile phase above a temperature of about 0° C. For example, the heating element 63 can supply enough thermal energy to prevent or minimize the effects of freezing within the static pressure regulator 61. In some embodiments, heating element 63 can supply enough thermal energy to keep the mobile phase at ambient temperature. In certain embodiments, the heating element 63 can supply enough thermal energy to keep the mobile phase at a temperature at or above the dew point temperature of the system 10. As a result, condensation on system 10 is substantially reduced or minimized To heat the static pressure regulator, the heating element 63 is placed in thermal contact with the static pressure regulator 61. To position and hold heating element 63 in contact with static pressure regulator, block 212 secures the heating element 63 and static regulator 61 together. In some embodiments (not shown), the heating element 63 can extend pass a second end 215 of the static pressure regulator 61. Some embodiments include more than one (e.g., two, three, four) heating elements 63 to heat the static pressure regulator 61.

Figure 9:
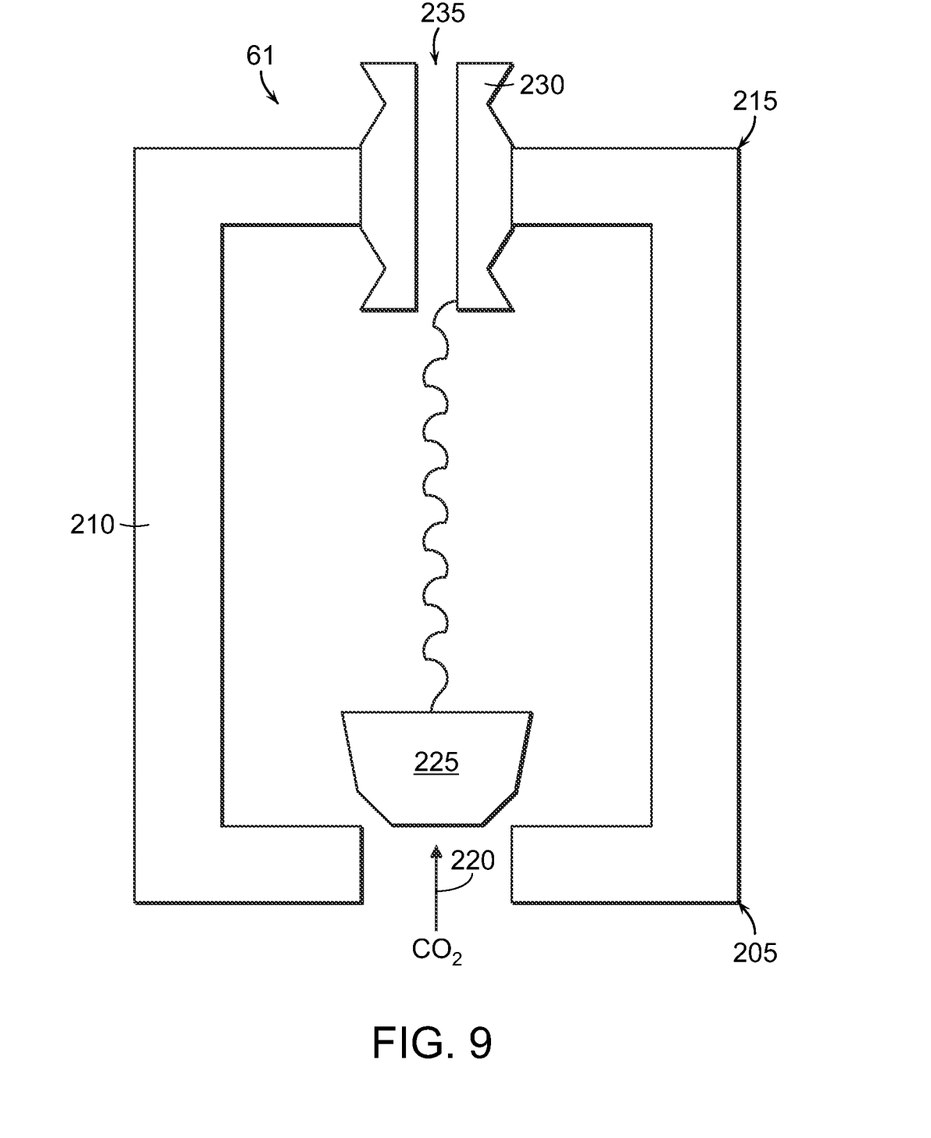
FIG. 9 represent a static pressure regulator according to one embodiment of the present disclosure.

Referring to FIG. 9, static pressure regulator 61 is a passive pressure regulator. That is, the pressure of the static pressure regulator 61 is set and does not change during an operative run of system 10. In embodiments, the pressure at inlet 220 is set above the critical pressure of the mobile phase media. For example, in some embodiments, the pressure at inlet 220 is set to a pressure falling within a range of about 1500 to 1070 psi. In other embodiments, the pressure is set within a range of about 1400 to 1150 psi, for example, 1250 psi.

To set the pressure of static pressure regulator 61, the static pressure regulator 61 is fitted with screw 230. In an exemplary embodiment, the mobile phase, such as $CO_2$, passes through inlet 220 and pushes on poppet 225. Screw 230 is adjusted to set the desired pressure to attain constant pressure on poppet/coil 225. The mobile phase move around the poppet 225 and exits through a hole 235 in the center of the screw 230. Other exit paths, in addition to, or alternative of hole 235 are possible.

By setting the pressure of the static pressure regulator 61 to a pressure above the critical pressure, the mobile phase media is maintained in a single phase (e.g., liquid phase) in the dynamic pressure regulator 57. As a result, the dynamic pressure regulator is not exposed to a phase change, nor is it exposed to a dual phase or multiphase (e.g., combination of liquid and gas phase) material. In general, dynamic pressure regulators can more consistently control the pressure of a single phase material (e.g., a material having a substantially constant density). Therefore, by maintaining the phase of the mobile phase media as a liquid throughout the dynamic pressure regulator, improvements in pressure control can be achieved.

In addition to advantageous pressure control, the two stage pressure regulator of the present technology also provides advantageous thermal regulation. For example, a phase change from a liquid to a gas is an endothermic reaction, which results in localized freezing. By restricting the location of the phase change to the static pressure regulator 61, the damaging effects of freezing are localized (e.g., freezing occurs only within the location of the phase change—the static pressure regulator 61). Heating efforts can therefore also be localized to the static pressure regulator 61, thereby simplifying heating requirements. In addition, in the event that that the heating element 63 is unable to counteract the damaging effects of the endothermic reaction, only the inexpensive static pressure regulator 61 needs to be repaired or replaced, rather than the more expensive dynamic pressure regulator 57.

As described in the foregoing figures, the static pressure regulator is generally set to a pressure above the critical pressure of the mobile phase, thereby guaranteeing that the mobile phase, such as $CO_2$, is liquid through the dynamic regulator. The dynamic regulator can control pressure more consistently when the mobile phase is liquid on both the inlet and the outlet. If at the outlet of the dynamic pressure regulator a gas exists, small reductions in restriction can cause the mobile phase, e.g., $CO_2$, to gasify upstream of the dynamic pressure regulator causing it to be unable to accurately control pressure. In addition, the static pressure regulator is guaranteed to be the location of phase change. Because the phase change of $CO_2$ is endothermic, controlling the phase change location prevents condensation, frost, clogging and sputtering, and pressure disturbances and fluctuations throughout the pressurized flow system.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other functions and advantages are also within the scope of the invention.

What is claimed is:

1. A method for controlling the pressure of a mobile phase in a chromatographic system, comprising:
 passing a mobile phase downstream of a chromatography column into a first regulator in a first phase state;
 varying the pressure inside said first regulator while maintaining the first phase state;
 passing the mobile phase into a second regulator downstream of the first regulator, wherein the second regulator is an adjustable regulator configured to be set to maintain a desired pressure upstream of the second regulator, wherein the second regulator includes a body, an inlet, an outlet, a poppet/coil, and a screw configured to set a desired pressure for the poppet/coil;
 wherein fluid composition at the first regulator is the same as fluid composition at the second regulator;

causing the first phase state to change to a second phase state different from the first phase state in the second regulator;

heating an element, before said second regulator, within said second regulator, or after said second regulator, or a combination thereof, to an internal temperature sufficient to keep said mobile phase above a temperature of about 0° C.; and passing said mobile phase proximate said element.

2. The method of claim 1, wherein the heating is before the second regulator.

3. The method of claim 1, wherein the heating is within the second regulator.

4. The method of claim 1, wherein the heating is before the second regulator and within the second regulator.

5. The method of claim 1, wherein the mobile phase comprises CO2.

6. The method of claim 1, wherein the first phase state is a supercritical phase state.

7. The method of claim 1, wherein the first phase state is a liquid phase state.

8. The method of claim 1, wherein the second phase state is a gas phase state.

9. The method of claim 1, wherein heating the element to the internal temperature keeps the mobile phase at a temperature above dew point temperature at the chromatographic system's location.

10. The method of claim 1, wherein the first regulator is a dynamic pressure regulator.

11. The method of claim 1, wherein the second regulator is a static pressure regulator.

12. The method of claim 1, wherein the second regulator is configured to maintain the desired pressure.

* * * * *